United States Patent [19]

Nobilet et al.

[11] Patent Number: 4,769,149
[45] Date of Patent: Sep. 6, 1988

[54] METHOD FOR THE RECOVERY OF ENERGY FROM WASTE AND RESIDUES

[75] Inventors: Bernard Nobilet, Bouc Bel Air; Michel Bonhomme, Montpellier; Philippe Desplat, Equilles, all of France

[73] Assignee: Propiorga, Puyricard, France

[21] Appl. No.: 95,604

[22] PCT Filed: Dec. 4, 1986

[86] PCT No.: PCT/FR86/00418
§ 371 Date: Aug. 4, 1987
§ 102(e) Date: Aug. 4, 1987

[87] PCT Pub. No.: WO87/03575
PCT Pub. Date: Jun. 18, 1987

[30] Foreign Application Priority Data

Dec. 5, 1985 [FR] France ................ 85 18019

[51] Int. Cl.[4] .................. C02F 11/04; C05F 7/00; C05F 9/00
[52] U.S. Cl. ................... 210/603; 210/180; 71/10; 71/901; 48/197 A
[58] Field of Search ............. 71/10, 901, 11, 12, 71/13, 14; 210/603, 180, 188, 218; 48/197 A; 435/167

[56] References Cited

U.S. PATENT DOCUMENTS

| | | | |
|---|---|---|---|
| 1,892,681 | 1/1933 | Rankin | 210/188 |
| 3,577,229 | 5/1971 | Brück | 71/10 |
| 4,028,087 | 6/1977 | Schultz et al. | 71/901 |
| 4,076,515 | 2/1978 | Rickard | 210/603 |
| 4,198,211 | 4/1980 | Shattock | 210/603 |
| 4,369,194 | 1/1983 | Arsovic | 210/603 |
| 4,632,758 | 12/1986 | Whittle | 210/180 |

FOREIGN PATENT DOCUMENTS

| | | | |
|---|---|---|---|
| 3036370 | 5/1982 | Fed. Rep. of Germany . | |
| 2249789 | 3/1975 | France . | |
| 2500990 | 10/1982 | France . | |
| 2521976 | 8/1983 | France | 210/603 |
| WO87/03575 | 3/1987 | PCT Int'l Appl. . | |
| 836829 | 3/1984 | U.S.S.R. | 71/10 |

Primary Examiner—Benoit Castel
Attorney, Agent, or Firm—Fisher, Christen & Sabol

[57] ABSTRACT

A process for recovery of energy from waste and residues is disclosed. The residues, after sieving, are subjected to bacterial digestion in a methanization reactor and the solid phase of the digestate is then subjected to incineration in a furnace supplying a heat recuperator, the furnace being supplied with complementary combustible by the methane coming from the digester, while the circuit of the fumes downstream of the recuperator is used for heating by at least one secondary circuit, the magma in the course of treatment in the digester and/or the sludge separated from the digestate before recycling thereof towards the digester.

5 Claims, 1 Drawing Sheet

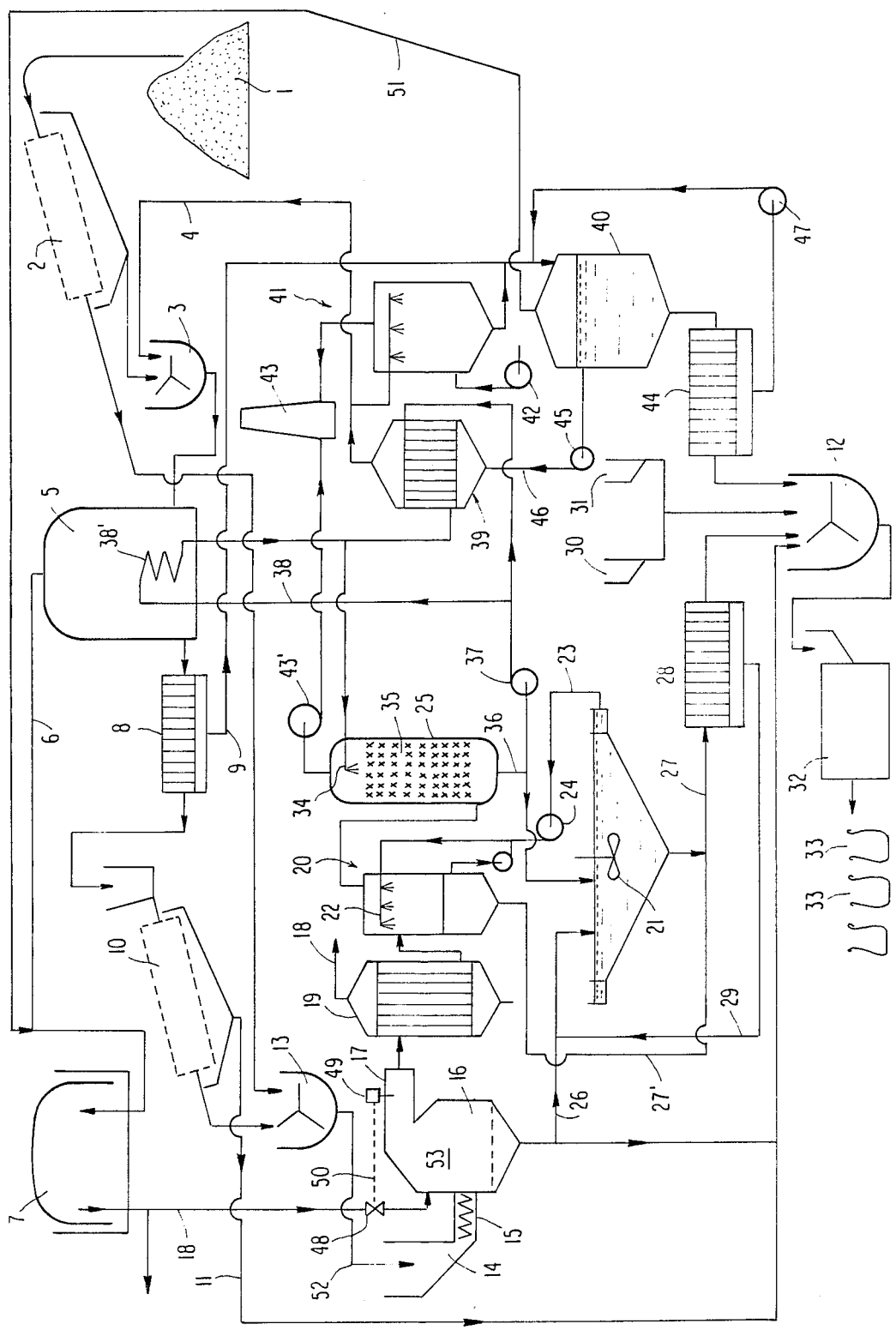

METHOD FOR THE RECOVERY OF ENERGY FROM WASTE AND RESIDUES

BACKGROUND OF THE INVENTION

The present invention relates to a process for total recovery of residues and waste of various origins, particularly residues of industrial or agricultural origin or urban refuse of the household garbage type.

SUMMARY OF THE INVENTION

The process according to the invention allows recovery of these by-products with production of energy, in particular in the form of combustible gas, and of thermal energy and with the obtaining of a product with added high value of the organo-mineral improvement or fertilizer type, and this without any rejection into the environment of polluting residues in the liquid, solid or gaseous state.

To that end, the invention relates to a process for recovery and exploitation of residues or rejects of industrial, agricultural or urban origin, with a view to extracting the potential energy therefrom, and characterized in that the residues, after sieving and separation of the fines, are subjected to an operation (known per se) of bacterial digestion in a methanization reactor with a view to producing a stored combustible gas, and in that the solid phase of the digestate coming from the preceding operation, after fresh sieving and separation of the fines, is subjected to incineration in a furnace in order to produce thermal energy recovered in at least one heat recuperator, the respective two steps of bacterial digestion and of incineration being joined together so that at least one of the two steps uses at least partially the production of energy of the other step, enabling the conditions of operation of the receiving step to be optimized.

Within the scope of embodiment of the process according to the invention, the waste is thus subjected to a first step of digestion with a view to producing combustible gases and to a subsequent step of incineration with a view to producing thermal energy.

For example, and in accordance with an important feature of the invention, there is used in the incineration phase, the energy of the combustible gas produced in the preceding methanization phase and, to this end, there is injected into the incineration furnace a quantity of combustible gas for the purpose of regulating the conditions of production of thermal energy during the incineration phase.

In particular, the injection of gas into the incineration furnace is modulated as a function of the regime of instantaneous operation of the furnace, depending on the calorific characteristics of the solid fuel which supplies it, the complementary supply of the combustible gas thus being called upon to compensate the momentary irregularities or deficiencies in calorific power of the principal combustible, so as to obtain a substantially constant thermal regime and an optimum post-combustion of the combustible elements supplying the furnace.

However, according to the invention, the synergy may operate in both ways and in the same way as the incineration phase is optimized by taking part of the energy and the products derived from the preceding methanization phase, this first methanization phase is itself optimalized thanks to the particularly calorific supply taken from the incineration phase.

In this way, the thermal energy produced in the incineration phase is used for heating the magma in the course of digestion in the methanization reactor and for optimizing production of combustible gas.

According to another feature, the thermal energy produced in the incineration phase is used for obtaining concentration of the sludge and liquors coming from the separation of the solid phase of the digestate, with a view to recycling thereof.

In addition, in order to obtain total recovery of the residues and waste, the invention allows production of a by-product of value, constituted by the solid particles adapted to form a substrate for agricultural or other use.

And to this end, the fines coming from the initial separation of the residues, then from the separation of the solid phase of the digestate, are mixed with the combustion ashes and with a solid phase coming from decantation of the sludge and liquors extracted from the digestate in order to constitute an organo-mineral horticultural improvement or fertilizer.

The invention also relates to an installation for carrying out the various characteristics of the processes set forth hereinabove, and characterized in that it comprises a digester for anaerobic fermentation of industrial, agricultural or urban waste or residues, with a view to producing methane, sieving means being disposed downstream of the digester to ensure separation within the solid phase of the digestate of the finest particles which are eliminated to constitute the basis of an organo-mineral fertilizer, a conveyor adapted to convey the coarser elements towards an incineration furnace provided with a post-combustion chamber comprising at least one gas burner supplied from a member for storing the methane such as a gas holder, coming from the methanization phase, the combustion gases supplying a heat recuperator.

Other characteristics and advantages of the invention will appear from the following description and which is given in connection with a particular embodiment presented by way of non-limiting examples and in the light of the accompanying drawings.

BRIEF DESCRIPTION OF THE DRAWING

The FIGURE shows a view of a skeleton diagram of the process and installation according to the invention.

DESCRIPTION OF THE PREFERRED EMBODIMENTS

The raw material is taken from heap 1 and conveyed towards a sieving or separating assembly possibly constituted as indicated by way of Example in the FIGURE by a first rotary sieve drum 2; that part intended to constitute the product subjected to digestion is collected in the mixer 3 where it receives via pipe 4 the recycled liquors removed downstream of the digester and constituting the liquid phase of the magma forming the effluent of the digester or digestate; the circuit for recycling the liquors extracted from the digestate being described hereinbelow.

The raw material leaving mixer 3 is conveyed by conveying means up to the methanization reactor or digester 5.

The gas collected at the top of the digester is conveyed via pipe 6 up to the storage gas holder 7.

The magma leaving the methanization reactor passes into a separating apparatus for example a filter press 8 from which the liquid phase or liquor is evacuated to be conveyed via pipe 9 towards the assembly for concentration-decantation of the liquors described hereinbelow.

The solid phase of the digestate formed by compact blocks on leaving the separation apparatus, for example the filter press 8, is broken up so as to resume a particulate state and to allow passage in a second sieving assembly constituted for example by a rotary sieve 10.

The finest particles or undersize are collected to constitute the basis of an organo-mineral fertilizer and they are conveyed via a conveying circuit 11 up to mixer 12. The coarsest particles or oversize leaving the sieve 10 are intended to constitute the combustible matter supplying the subsequent step or incineration step.

The oversize coming from the separation apparatus 10 for example a sieve is to this end homogenized in the mixer 13 with the oversize coming from the first sieving or separation assembly 2 and also constituted by coarser particles.

The combustible coming from the oversize of the separation assemblies is thus constituted by particles either refused at the first separation and not having transited through the digester or by particles coming from the digestate but having remained in a coarser granulometric state.

This assembly is composed of particulate debris, particularly pieces of paper or cardboard not totally digested in the digester, debris of wood or of vegetable elements, debris of plastics matter, bones, etc.

This material possesses an interesting calorific power and especially thanks to the high percentage of products extracted from the digester, this product possesses a homogeneity and controllable characteristics with the result that it constitutes a useful combustible allowing regularity and control of the supply of the incineration assembly.

This will allow a regular functioning of the incineration furnace opposing functioning in waves and jolts of the incineration furnaces supplied with ungraded waste whose characteristics are considerably irregular and bereft of any homogeneity as far as the composition, granulometry, hydrometry and consequently the calorific power are concerned.

To that end, it may be provided that virtually all the residues treated from the starting heap 1 will pass through the methanization phase in order to obtain the greatest regularity and a constant control in the characteristics of the combustible thus obtained.

The waste forming the combustible treated in the mixer 13 is conveyed towards the supply hopper 14 serving a supply conveyer, for example of the Archimedean screw type 15 or any other apparatus thus controlling the supply of the incineration furnace 16.

Combustion in this furnace is controlled so as to respect temperature references at each step of their oxidation by the presence of burners and of devices for regulating the combustion-supporting air.

This furnace comprises a post-combustion chamber 17 and gas burners 53 supplied from circuit 18 with methane coming from the storage gas holder 7.

The incineration furnace may be provided with probes 49 adapted permanently to analyze the operational parameters such as temperatures in the different zones of the furnace, composition of the fumes, etc. . . . and as a function of these parameters the supply of complementary gas from pipe 18 may be adjusted so as to overcome and compensate the slight sudden changes in operation which may exist taking into account the characteristics of the supply combustible.

Supply of a complementary combustible available in situ makes it possible to ensure automatization and permanent functioning of the whole of the installation without the presence of any service staff apart from a very limited surveillance and maintenance team.

Supply of complementary combustible gas may be regulated by an automatic valve 48 servo-controlled by a probe 49 via a circuit 50.

The combustion gases leaving the post-combustion chamber 17 at a temperature of the order of 900° to 1000° C. pass in a first heat recuperator formed for example by a tubular boiler 19 producing at 18 a heat-transfer fluid at high temperature such as dry steam or superheated water or any other thermal fluid; this heat-transfer liquid is directed towards the possible uses such as a turbine for producing electrical energy or any conventional use.

The combustion gases leaving recuperator 19 at a temperature of the order of 250° to 350° C. cannot be rejected into the atmosphere as they are strongly laden with anhydrides or acid vapours ($NO_2$, HCl and $SO_3$), these noxious products generally coming from the decomposition and combustion of plastics materials and generally synthetic materials (in particular PVC).

It is therefore impossible to reject these fumes into the atmosphere; furthermore, it is desirable to recover the latent heat and the sensible heat contained in these fumes which, on leaving the boiler 19, are still at a high temperature.

The installation described here comprises an assembly for washing the fumes with a view to neutralizing them at high temperature before these fumes are cooled to attain the dew point, beyond which would be formed the corrosive acids agressive for the metals constituting the enclosures of the installation.

The combustion ashes are thus poured into the vat 21 where they are placed in suspension or in solution to constitute a slurry with strongly basic pH which may be taken for example from a peripheral chute or any other system via the circuit 23 terminating in the spray pipe 22 of the neutralizing chamber 20.

Within the chamber 20, the liquid phase formed by the basic slurry described hereinabove encounters the acid vapours which are neutralized by terminating in the formation of generally insoluble salts which are sedimented to arrive via the evacuation circuits 27, 27' at the filter press 28; these salts, after draining, are poured into the mixer 12 where they encounter the fine particles coming from the digestate and constitute the basis of the organomineral fertilizer.

The incorporation in these fine particles constituting an improvement of the inorganic principles coming from the neutralizing assembly enriches the basis of the improvement with active principles, particularly nitrogen, phosphorus and potassium and makes it possible thus to obtain a rich improvement or a veritable organo-mineral fertilizer.

This latter may, as a function of the necessary adjustments, receive the incorporation of additives coming from hoppers 30 and 31 to obtain a constant richness in active principals.

The mixed, homogeneous assembly is conveyed from the mixer 12 towards the supply hopper of a bagging assembly 32 to be delivered in doses packed in the form of bags of organo-mineral fertilizers 33, 33'.

The purified gases leaving the neutralizing chamber 20 and strongly laden with water vapour may then be subjected to an operation of condensation in the condensation tower or condenser 25 where they encounter in counter-flow trickling water coming from the upper spray(s) 34.

The trickling water, enriched with the condensation water coming from the purified gases is collected hot at the base of the column 25 whence it is partially recycled towards the vat 21 whilst the major part is conveyed from the circulator 37 towards the secondary heat exchangers 38' and 39 respectively via the secondary circuit 38.

The effluent coming from the condensation tower 25 is in fact pure water taken to a temperature of the order of 60° C.; its sensible heat is recovered in the heat exchangers, respectively the first secondary heat exchanger 38' located within the magma in the course of treatment in the digester 5 and giving its calories to this magma in the course of fermentation, and the second secondary heat exchanger 39 belonging to the assembly for condensation and decantation of the liquors coming via pipe 9 from filtration at 8 of the digestate.

The heat exchanger 39 gives its calories to the filtration liquor of the digestate stored in the buffer reservoir 40 itself supplied via pipe 9; the reheated liquor sprayed at the top of the evaporator 41 where it encounters the ascending current of fresh air coming from the ventilator 42, the air laden with humidity being evacuated at the top of the evaporator 41 to be possibly directed towards the draught stack 43.

The buffer reservoir 40 may be arranged to constitute a secondary fermenter supplied with concentrated and reheated liquors and allowing production of methane joining via circuit 51 the storage reservoir 7.

The liquors thus concentrated and possibly having undergone a complementary fermentation are recycled via circuit 4 towards the mixer 3 for supplying the digester 5 whilst part of the liquors is returned to the buffer reservoir 40.

This buffer reservoir possibly comprises means allowing removal at its base of the solid sedimented particles which, after concentration in the separation apparatus, for example the filter press 44, are sent into the mixer 12 to enrich the organo-mineral fertilizer, particularly with nitrogenous matter, the liquid phase of filtration being recycled by pump 47 towards the reservoir 40.

According to a development of the invention, the gaseous effluents leaving the digester 5 and/or the secondary fermenter 40 are purified before joining the gas holder 7 in order to separate a first phase rich in methane from a second phase constituted mainly by air and carbon monoxide; this latter phase is, however, not rejected into the atmosphere as it still contains a small percentage (of the order of 4 to 5%) of methane; this second phase is therefore injected into the incineration burner 16 where the air that it contains constitutes the combustion-supporting gas whilst the methane and possibly the carbon monoxide are recovered and burnt, thus completing exhaustion of the potential thermal energy contained in the starting raw material.

We claim:

1. In a process for recovery and exploitation of a starting material comprising solid residues or rejects of industrial, agricultural or domestic origin, of the type in which the residues are subjected to an operation of bacterial digestion in a methanization digester for the production of a recovered and stored combustible gas, while a solid phase of digestate leaving the digester is subjected to incineration in a furnace for the purpose of producing thermal energy, and in which the conditions of incineration are improved by injecting into the furnace part of the gas coming from the methanization digester and the conditions of production of methane are improved by using the heat of the furnace to heat in the course of bacterial digestion, and the process further comprising the following successive steps of:

(a) separating by sieving within the starting material the coarsest particles from the finest particles, conveying the coarsest particles to the furnace and the finest particles to the digester;

(b) mixing in a mixer said finest particles with a liquid phase constituted by liquors separated from the digestate leaving the methanization digester;

(c) allowing the finest particles to stay in the methanization digester while supplying an addition of calories to accelerate the digestion, and storing the combustible gas produced in a gasometer;

(d) separating by filtration within the digestate leaving the digester a solid phase from a liquid phase constituting the liquors, and recycling said liquors to the mixer in accordance with step (b) hereinabove;

(e) subjecting the solid phase of the digestate to decompacting and sieving, separating the finest particles forming an undersize phase and directing the coarsest particles or oversize with the coarsest particles from the sieving of step (a) towards the incineration furnace to constitute the principal solid fuel supplying said furnace;

(f) monitoring at all times the parameters of combustion within said furnace, including temperature, and introducing into the furnace a metered quantity of combustible gas coming from the gasometer, in response to the data observed, in order to supplement the calorific power of the principal solid fuel, thus regulating the conditions of combustion;

(g) causing combustion fumes coming from said furnace to pass into a first heat recuperator to produce a high-temperature heat-bearing fluid, which is used for industrial purposes;

(h) washing the fumes on leaving the first heat recuperator by neutralization by means of a basic milk coming from combustion ashes suspended in an aqueous phase;

(i) collecting said milk on leaving the neutralization step according to (h) hereinabove and separating the solid phase, which is mixed with the undersize phase coming from the sieving of step (e) hereinabove, to constitute an organo-mineral improvement for the soil;

(j) conveying purified gases leaving the neutralization step according to (h) hereinabove into a second heat recuperator delivering a heat-bearing fluid conveyed towards a heat exchanger located within the methanization digester, thus constituting the supply of calories of step (c) hereinabove.

2. Process according to claim 1 wherein the thermal energy coming from the incineration furnace and conveyed by the heat-bearing fluid coming from the second heat recuperator is used for concentrating the liquors coming from the separation of the solid phase from the digestate, and recycling said concentrated liquors to the digester.

3. Process according to claim 1 wherein the thermal energy coming from the incineration furnace and contained in the heat-bearing fluid coming from the second heat recuperator is used for heating and concentrating the liquid liquors separated from the digestate, which are introduced in liquid phase into a second or secondary digester for the production of an auxiliary flow of methane.

4. Process according to claim 1 wherein the finest particles forming the undersize phases of sieving step (e) hereinabove, are mixed in a second mixer with (i) solid residues obtained from sedimentation of the neutralization milk and (ii) solid residues obtained by decanting the digestate to form an organo-mineral horticultural improvement or fertilizer.

5. Process according to claim 4 wherein residues (i) and (ii), before mixing with said finest particles (e) are subjected to elimination of glass objects therein and crushing the glass object until a pulverulent, sandy phase and introducing such sandy phase into said second mixer to obtain a complete culture substrate.

* * * * *